United States Patent [19]
Cronje et al.

[11] Patent Number: 5,204,368
[45] Date of Patent: Apr. 20, 1993

[54] BACTERIOSTATIC AND BACTERIOCIDAL METHOD USING FULVIC ACID DERIVATIVES

[75] Inventors: Izak J. Cronje, Verwoerdburg; Thomas E. Cloete, Pretoria; Johannes Dekker, Pretoria; Hendrik Swart, Pretoria, all of South Africa

[73] Assignee: National Energy Council, Transvaal, South Africa

[21] Appl. No.: 696,710

[22] Filed: May 7, 1991

[30] Foreign Application Priority Data

May 25, 1990 [ZA] South Africa .................. 90/4033

[51] Int. Cl.$^5$ ............................................. A01N 43/16
[52] U.S. Cl. ................................................... 514/455
[58] Field of Search .............................. 514/763, 455

[56] References Cited
PUBLICATIONS

Yamauchi et al., "Studies on the Synthesis ... ", Chem. Abst. 107(25):236301 (1987).
Tichy et al., "Biological Activity of Humus Acids Isolated ... ", Chem. Abst. 82(21):135999 (1975).

Primary Examiner—Frederick E. Waddell
Assistant Examiner—Gregory Hook
Attorney, Agent, or Firm—Cushman, Darby & Cushman

[57] ABSTRACT

The present invention relates to compounds of the class of coal-derived fulvic acid or a salt or a derivative thereof as active ingredient in a suitable carrier, useful as a bactericidal or bacteriostatic agent. The carrier is preferably water.

9 Claims, 5 Drawing Sheets

BACTERIOSTATIC AND BACTERIOCIDAL METHOD USING FULVIC ACID DERIVATIVES

BACKGROUND OF THE INVENTION

This invention relates to a composition which has bactericidal or bacteriostatic activity.

There is a great demand both in industry and elsewhere for agents which have bactericidal activity or bacteriostatic activity or both. An agent which has bactericidal activity will destroy bacteria whereas an agent which has bacteriostatic activity will inhibit the growth of bacteria without destroying them. Examples of industrially used bactericidal agents are phenol and its derivatives, hypochlorite, mercuric chloride and organic mercury compounds. Many of these agents are specialist chemicals which are expensive.

British Patent Publication No. 2215603 describes the use of coal-derived humic acids and salts thereof as a bactericidal and bacteriostatic agent.

SUMMARY OF THE INVENTION

According to the present invention, there is provided a composition having bactericidal or bacteriostatic activity comprising an agent selected from coal-derived fulvic acid, salts and derivatives thereof, and a suitable carrier.

Further according to the invention, there is provided a method of reducing the bacterial activity of a locus including the step of applying a composition as described above to that locus.

DETAILED DESCRIPTION OF THE INVENTION

Figure 1:
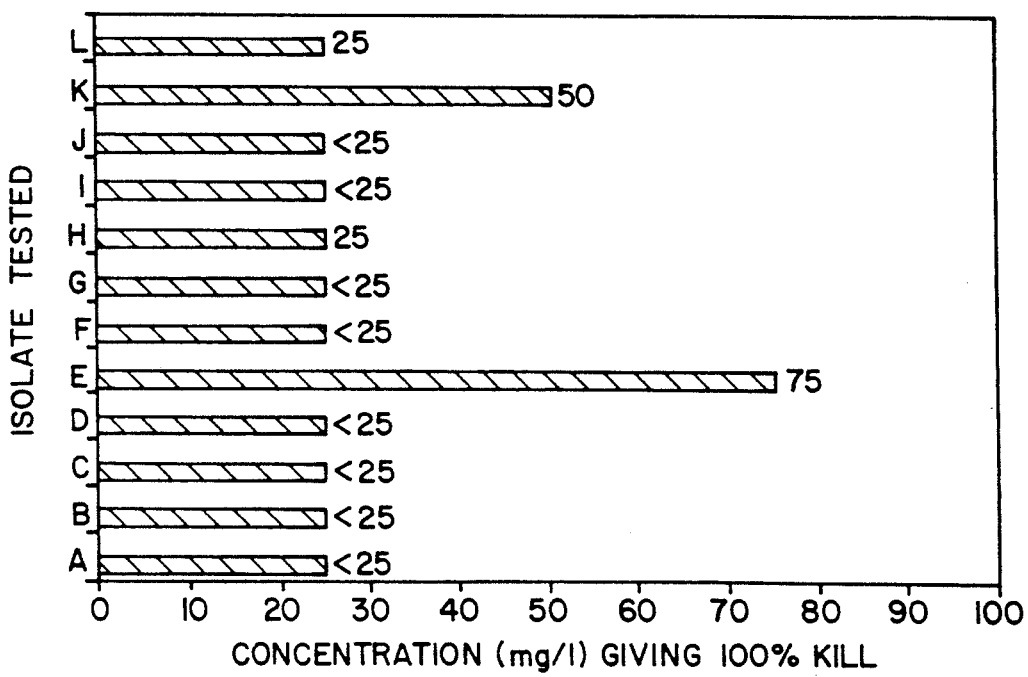
Figure 2:
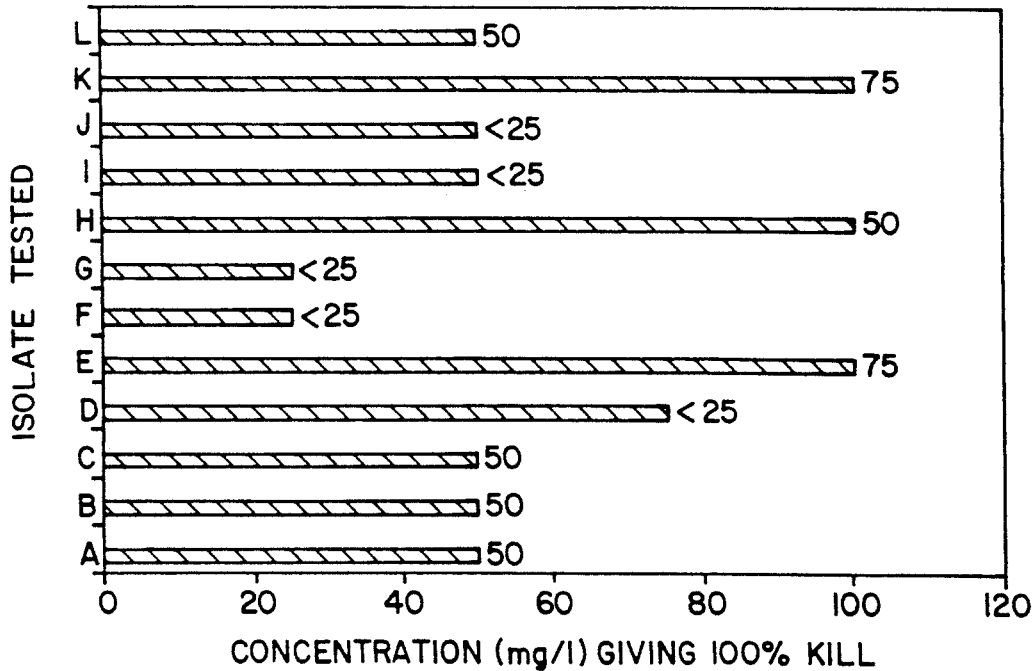
Figure 3:
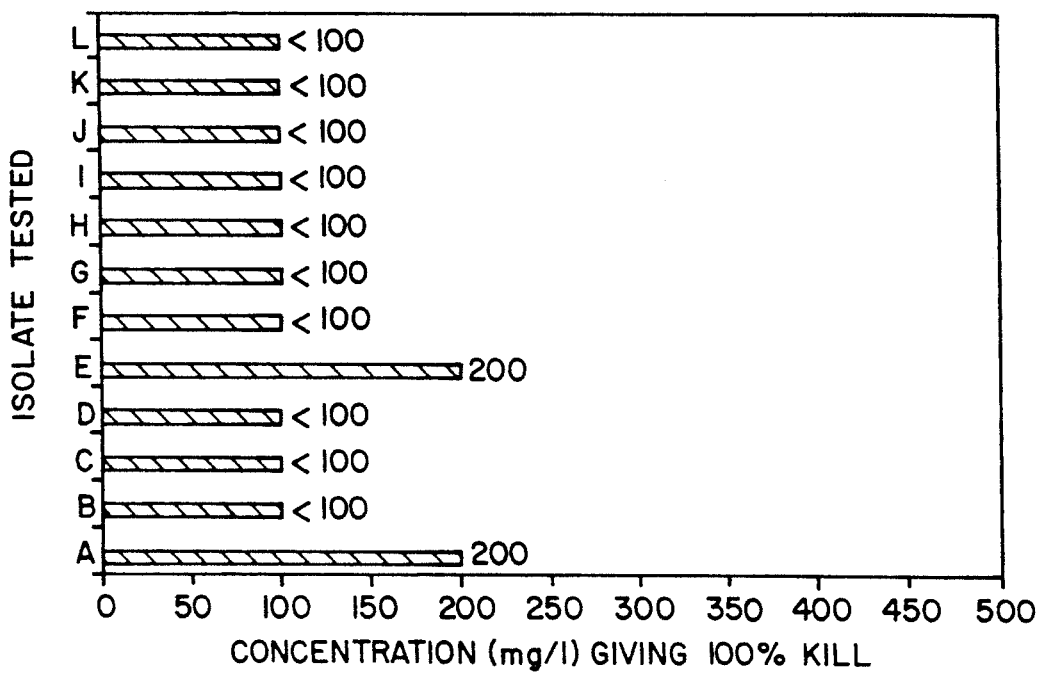
Figure 4:
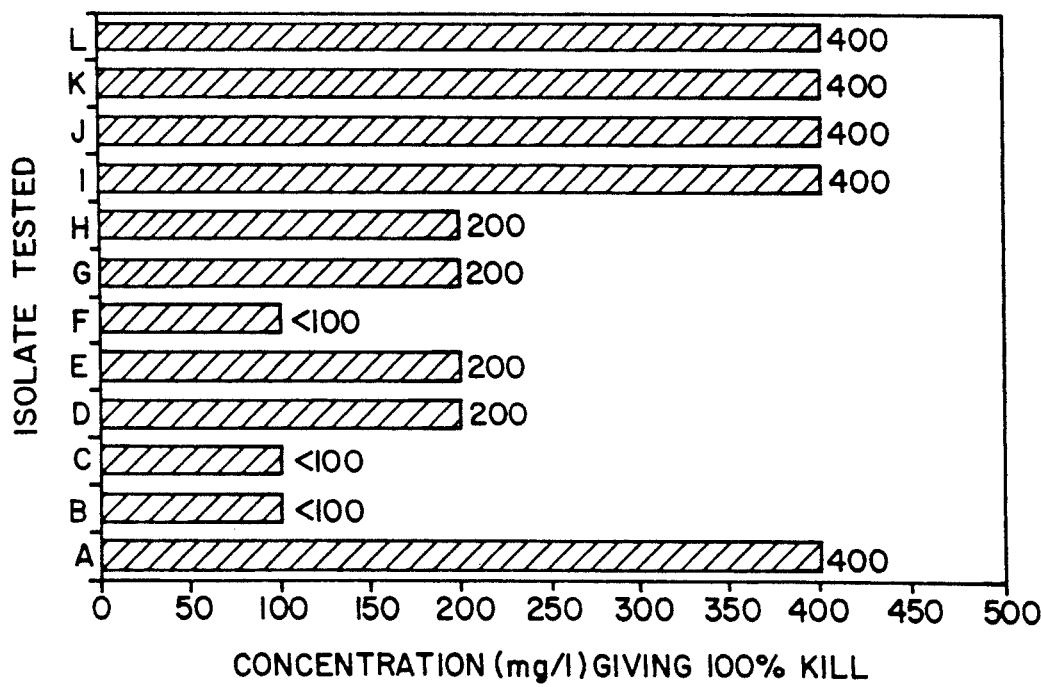
Figure 5:
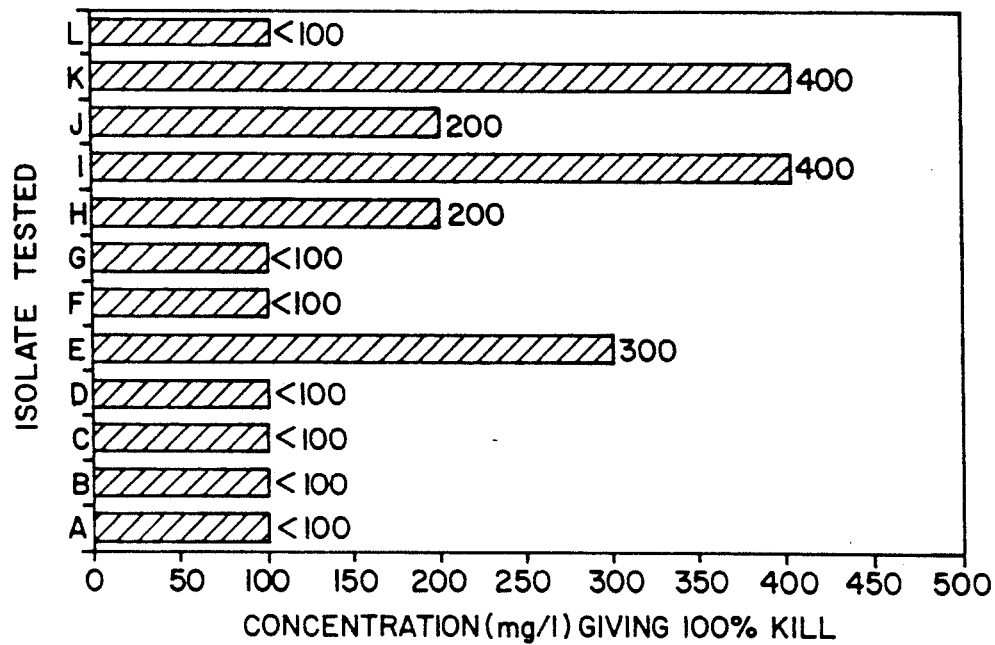

Essential to the invention is that the fulvic acid is coal-derived, i.e. is produced during the wet phase oxidation of coal. Coal, as is known, is a carbonaceous rock originating from plant organic material which has been formed by temperature and pressure, and a variety of chemical processes during a so-called "coalification" period. Preferably, the coal is one with a rank ranging from lignite/brown coal to bituminous hard coal.

The fulvic acid, as mentioned above, is produced during the wet phase oxidation of coal, preferably the process described and claimed in U.S. Pat. No. 4,912,256. The method of this United States patent involves mixing the coal with an aqueous medium to produce a slurry having a pH in the range 4 to 9, reacting the slurry with a gaseous oxidant selected from oxygen, air and mixtures thereof under conditions of temperature and pressure and for a period sufficient to cause the oxidation of the coal thereby producing an oxidised coal containing humic acids and fulvic acids dissolved in the aqueous medium and separating the oxidised coal from the aqueous medium. The aqueous medium may be concentrated. Also, the fulvic acids may be extracted from the aqueous medium using organic solvents such as butanone and methanol.

Coal-derived fulvic acid will generally have the following elemental analysis and/or functional group analysis, both on an air-dried basis:

| Element | Range (%) |
|---|---|
| Carbon | 10-70 (typically 20-45) |
| Hydrogen | 1-6 (typically 2-4) |
| Nitrogen | 1-4 (typically 2-3) |
| Oxygen | 10-70 (typically 40-60) |

| Functional Group | Range (meq/g) |
|---|---|
| Total acidity | 2-24, typically 11,8 |
| Carboxylic | 2-24, typically 10,7 |
| Phenolic | 0.1-12, typically 1,1 |

The composition may take a liquid or solid form, depending on the carrier. When the carrier is liquid, it is preferably an aqueous carrier. In this form, the composition may be used as a household or industrial disinfectant. The composition with an aqueous carrier has been found to be particularly suitable in disinfecting water in cooling towers or the cascade plates over which water in such towers passes. The composition may also be used in the form of a soap or other suitable solid form.

When an aqueous carrier is used, the pH of that medium containing agent and carrier will generally be in the range 0.5 to 12, preferably 7 to 8.5.

The concentration of the agent in the composition will vary according to the nature of the application. Generally, the concentration of the agent will be in the range 0.1 to 99 percent by weight.

The composition can be used to reduce the bacterial activity of a locus to which it is applied. The action of the composition will be bactericidal at higher concentrations of the agent and bacteriostatic at lower concentrations. In both situations, the bacterial activity of the locus is reduced.

The invention will now be illustrated by the following examples and trials.

PREPARATION

Fulvic acid was derived from a bituminous coal which had been oxidised by the following process:

Coal (200 g) and water (400 ml) were slurried in a 2 liter stirred reactor. The reactor was pressurised to 8,0 MPa with oxygen, heated with external bar heaters to 200° C. Oxygen was allowed to flow through the slurry at a rate of 4 liters/minute. After one hour the oxygen flow was terminated, the reactor cooled down to room temperature and the pressure released to atmospheric.

The slurry consists of oxidised coal (insoluble in water and hereinafter referred to as "oxicoal") and a solution of fulvic acid (hereinafter referred to as "oxifulvic acid") in water. By filtration, the oxicoal was separated from the solution of oxifulvic acid in water. The concentration of the oxifulvic acid in water was determined to be 8.45% (on a mass per volume basis). The oxifulvic acid is recovered by drying the aqueous oxifulvic acid solution.

The oxifulvic acid exhibited the following analysis (on an air-dried basis):

| Elemental | Percentage |
|---|---|
| C | 30,0 |
| H | 2,8 |
| N | 3,2 |
| O | 63,9 |

| Functional Groups | Amount (meq/g) |
|---|---|
| Total acidity | 11,8 |
| Carboxylic | 10,7 |
| Phenolic | 1,1 |

This oxifulvic acid will hereinafter be referred to as a raw oxifulvic acid. In a similar manner, another raw oxifulvic acid was produced save that the oxidant used was not oxygen but air.

The bactericidal properties of oxifulvic acid in various forms was evaluated in trials which will be described hereinafter. In these trials, various forms of oxifulvic acid and known biocides were used and are identified in Table I below.

TABLE I

| | |
|---|---|
| I | Raw oxifulvic acid, prepared at 200° C. and air oxidised |
| II | Raw oxifulvic acid, prepared at 200° C. and oxygen oxidised |
| III | Raw oxifulvic acid of I concentrated to about 10% |
| IV | Oxifulvic acid produced from a methanol extract of II |
| V | Oxifulvic acid produced from a butanone extract of II |
| Bio Met | an industrial biocide |
| Met | methanol, chemically pure |
| But | butanone, chemically pure |

METHODOLOGY FOR EVALUATION OF BIOCIDAL ACTIVITY

The ability of coal-derived fulvic acid to inhibit the growth of bacteria was examined. The typical procedure followed was as follows:

The bacterial cultures were suspended in quarter strength Ringers solution to yield an initial bacterial number in excess of $10^6$ bacterial cells/ml. Each biocide was evaluated separately using a pure culture of each organism. The initial bacterial count of the culture suspension was determined using the standard spread plate technique. Standard I Agar (Merck) was used and incubation took place at 37° C. for 48 hours. Thereafter, biocide was added to the culture suspension and bacterial counts were repeated after 6 hours. A control was included for each individual culture. The percentage kill was calculated as follows:

$$\% \text{ kill} = 100 - \left( \frac{\text{survival count}}{\text{initial count}} \right) \times 100$$

1. TRIALS

The above mentioned procedure was followed, in duplicate, for every organism tested. The following two organisms were tested:

Pseudomonas aeruginosa
Staphylococcus aureus

The results obtained were as follows:

Evaluation of air-dried oxifulvic acid (derived from preparation II) as biocide

| Concentration (ppm) | Organism | % Kill after 6 hours |
|---|---|---|
| 100 | Pseudomonas | 51,2 |
| 200 | aeruginosa | 100 |
| 300 | | 100 |
| 400 | | 100 |
| 600 | | 100 |
| 800 | | 100 |
| 100 | Staphylococcus | 87,8 |
| 200 | aureus | 100 |
| 300 | | 100 |
| 400 | | 100 |
| 600 | | 100 |
| 800 | | 100 |

From the above results it is clear that the air-dried oxifulvic acid is an extremely effective biocide.

2. In a series of trials, the oxifulvic acids I to V above were tested against a wide range of bacteria set out in Table II below:

TABLE II

| Bacteria | Code |
|---|---|
| Staphlylococcus aureus | A |
| Pseudomonas aeruginosa | B |
| P. alcalisc | C |
| P. mendocina | D |
| P. pauciniobilus | E |
| P. picketti | F |
| P. stutzeri | G |
| P. fluroescens | H |
| P. vesicularis | I |
| P. cepacia | J |
| Alcaligenes xylooxidans | K |
| Acinetobacter calcoaceticus | L |

The results obtained are set out graphically in the attached FIGS. 1 to 5. It is apparent from these results that product I is the most effective bactericide of the five products.

Figure 6:
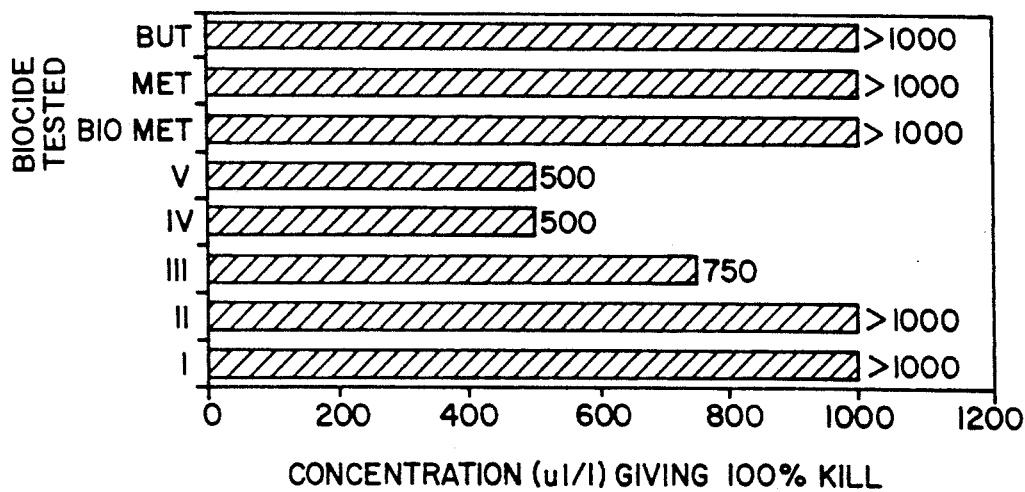
Figure 7:
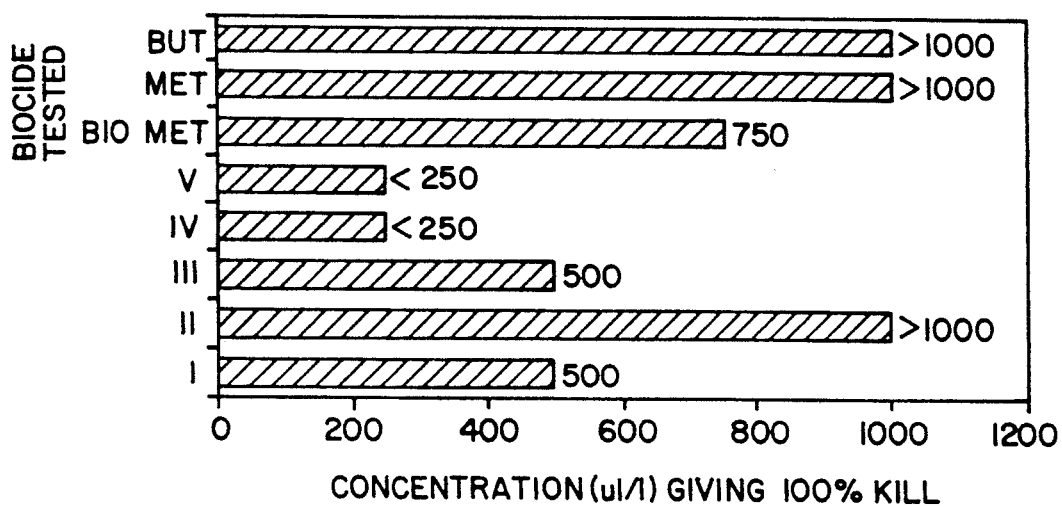

3. In a further trial, the various oxifulvic acids were evaluated as biocides against P. aeruginosa in ringers and against Staphylococcus aureus in ringers. The effectiveness of these oxifulvic acids was compared with butanone, methanol and Bio Met and the results obtained are set out graphically in FIGS. 6 and 7. It is again apparent that the oxifulvic acids of the invention compare favourably with these other known biocides and in many instances exhibit a more powerful biocidal activity.

4. The growth and proliferation of microorganisms in an industrial water cooling system may cause severe problems. The problems are associated with microbial growth namely, biofouling and biocorrosion. Biofouling of systems leads to increased fluid friction, reduced heat transfer and may cause or accelerate corrosion of the system. Biocorrosion in a system reduces process efficiency and equipment service life, with major economic consequences.

Figure 8:
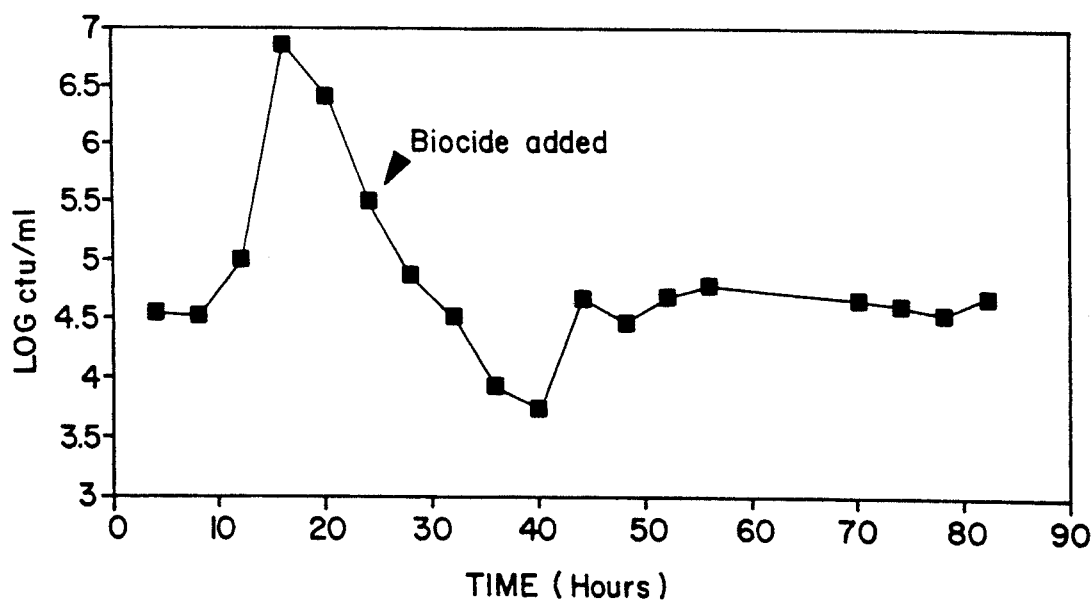
Figure 9:
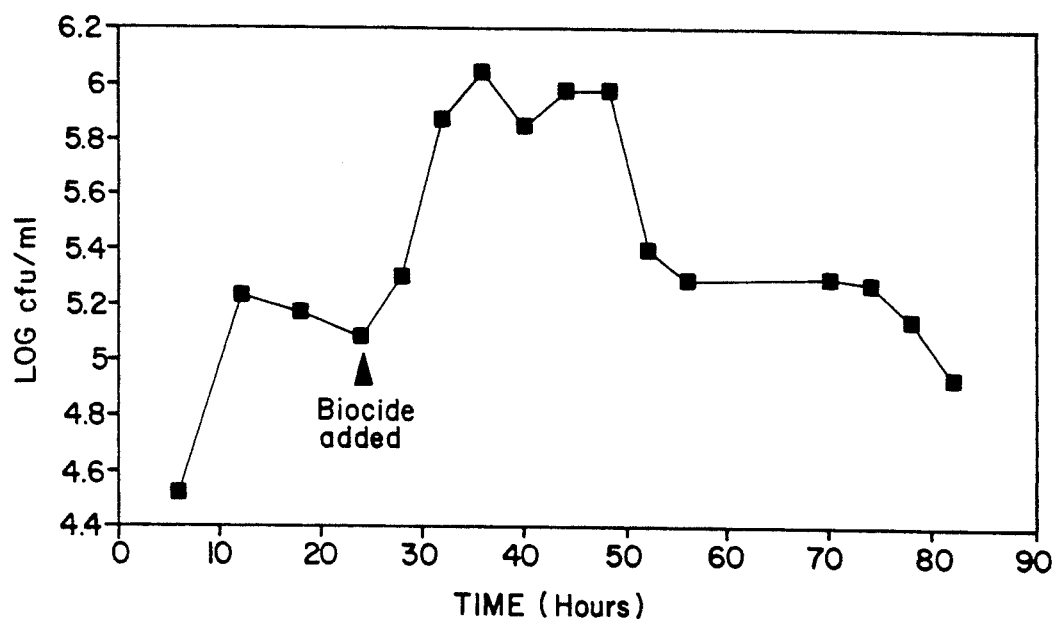

The use of bactericides is one of the most effective ways to prevent biofouling and the concomitant corrosion. In a field trial, it was found that oxifulvic acid I was more effective in controlling the growth and proliferation of microorganisms in industrial water cooling systems than Bio Met. The results are set out graphically in the attached FIGS. 8 and 9. In these graphs the lower the log cfu/ml value the more effective the biocide.

We claim:

1. A method of reducing the bacterial activity of a locus comprising administering to the locus an effective amount of a composition having bactericidal and bacteriostatic activity comprising an agent selected from the group consisting of coal-derived fulvic acid, salts and derivatives thereof, and a suitable carrier.

2. A method according to claim 1 wherein the coal is one with a rank ranging from lignite/brown coal to bituminous hard coal.

3. A method according to claim 1 wherein the fulvic acid has the following elemental analysis on an air-dried basis:

| Element | Range (%) |
|---|---|
| Carbon | 10–70 |
| Hydrogen | 1–6 |
| Nitrogen | 1–4 |

-continued

| Element | Range (%) |
|---|---|
| Oxygen | 10–70 |

4. A method according to claim 1 wherein the fulvic acid has the following elemental analysis on an air-dried basis:

| Element | Range (%) |
|---|---|
| Carbon | 20–45 |
| Hydrogen | 2–4 |
| Nitrogen | 2–3 |
| Oxygen | 40–60 |

5. A method according to claim 3 wherein the fulvic acid has the following functional group analysis on an air-dried basis:

| Functional Group | Range (meq/g) |
|---|---|
| Total acidity | 2–24 |
| Carboxylic | 2–24 |
| Phenolic | 0.1–12 |

6. A method according to claim 3 wherein the fulvic acid has the following elemental analysis on an air-dried basis:

| Functional Group | Amount (meq/g) |
|---|---|
| Total acidity | 11,8 |
| Carboxylic | 10,7 |
| Phenolic | 1,1 |

7. A method according to claim 1 wherein the carrier is a liquid carrier.

8. A method according to claim 7 wherein the liquid carrier is an aqueous carrier.

9. A method according to claim 8 wherein the pH of the medium containing the agent and carrier is in the range 7 to 8.5.

* * * * *